United States Patent [19]

Furutani et al.

[11] Patent Number: 5,395,972
[45] Date of Patent: Mar. 7, 1995

[54] PROCESS FOR PRODUCING AMINES

[75] Inventors: Atsushi Furutani, Nishinomiya; Takuo Hibi, Toyonaka; Michio Yamamoto, Otsu; Gohfu Suzukamo, Suita, all of Japan

[73] Assignee: Sumitomo Chemical Company, Limited, Osaka, Japan

[21] Appl. No.: 194,329

[22] Filed: Feb. 8, 1994

[30] Foreign Application Priority Data

Feb. 8, 1993 [JP] Japan ................. 5-020134

[51] Int. Cl.$^6$ ............................. C07C 209/26
[52] U.S. Cl. .................... 564/446; 546/244; 548/411; 564/248
[58] Field of Search ............. 564/446, 248; 546/244; 548/411

[56] References Cited

U.S. PATENT DOCUMENTS

| | | | |
|---|---|---|---|
| 4,041,080 | 8/1977 | Göthel et al. | 260/585 B |
| 4,206,149 | 6/1980 | Slaugh | 260/583 R |
| 4,206,150 | 6/1980 | Slaugh | 252/465 |
| 4,429,157 | 1/1984 | Disteldorf et al. | 564/446 |
| 5,166,396 | 11/1992 | Hutchmacher et al. | 558/431 |
| 5,166,444 | 11/1992 | Hutchmacher et al. | 564/491 |
| 5,239,120 | 8/1993 | Merger et al. | 564/454 |

FOREIGN PATENT DOCUMENTS

| | | |
|---|---|---|
| 2015251 | 10/1990 | Canada . |
| 2015252 | 10/1990 | Canada . |
| 2039328 | 10/1991 | Canada . |
| 0033529 | 8/1981 | European Pat. Off. . |
| 0394967 | 10/1990 | European Pat. Off. . |
| 0394968 | 10/1990 | European Pat. Off. . |
| 0530696 | 9/1991 | European Pat. Off. . |
| 0449089 | 10/1991 | European Pat. Off. . |
| 0503246 | 9/1992 | European Pat. Off. . |
| 3011656 | 10/1981 | Germany . |
| 62-123154 | 11/1985 | Japan . |
| 43-00852 | 3/1991 | Japan . |
| 50-85991 | 9/1991 | Japan . |
| 5-279303 | 10/1993 | Japan . |
| 5-301847 | 11/1993 | Japan . |
| 972010 | 10/1964 | United Kingdom . |
| 1554516 | 10/1979 | United Kingdom . |

OTHER PUBLICATIONS

Patai, The Chemistry of the Carbon-Nitrogen Double Bond; Wiley: New York, 1970, pp. 61-69.

March, Advanced Organic Chemistry; Wiley: New York, 1992, pp. 896-899.

"Chemical Abstracts" vol. 80, 1974-p. 384, abstract No. 145377g.

Chem. Abs. 118:38503j, Sep. 1992.

*Primary Examiner*—Glennon H. Hollrah
*Assistant Examiner*—Scott C. Rand
*Attorney, Agent, or Firm*—Birch, Stewart, Kolasch & Birch

[57] ABSTRACT

Amines are produced in high yield by the process which comprises allowing a cyclic ketone to react with ammonia in the presence of active carbon to produce imino derivatives and then, allowing the imino derivatives to react with hydrogen in the presence of a hydrogenating catalyst.

25 Claims, No Drawings

PROCESS FOR PRODUCING AMINES

The present invention relates to a process for producing amines and more particularly, to a process for producing amines which comprises allowing cyclic ketones to react with ammonia in the presence of active carbon to produce imino derivatives of the ketones and then allowing the imino derivatives to react with hydrogen in the presence of a hydrogenating catalyst.

Amines are useful as intermediates for fine chemicals and raw materials for resins and are well known to be produced by reductive amination of cyclic ketones. For example, for production of 3-aminomethyl-3,5,5-trimethylcyclohexylamine (IPDA) by reductive amination of 3-cyano-3,5,5-trimethylcyclohexanone (IPCN), the following processes have been known. ① A one-step process which comprises allowing IPCN to react with ammonia and hydrogen in the presence of a hydrogenating catalyst such as Raney cobalt (Japanese Patent Kokai No. 62-123154). ② A two-step process which comprises allowing IPCN to react with ammonia in the presence of an ion exchanger such as sulfonated polystyrene to produce an imino derivative and then allowing the resultant imino derivative to react with hydrogen in the presence of a hydrogenating catalyst (U.S. Pat. No. 4,429,157). ③ A two-step process which comprises allowing IPCN to react with ammonia in the presence of an acidic metal oxide such as alumina to produce an imino derivative and then allowing the resultant imino derivative to react with hydrogen in the presence of a hydrogenating catalyst (Japanese Patent Kokai No. 4-221350).

However, the one-step process ① has the defects that a reduction reaction of carbonyl group also takes place to produce a large amount of alcohols as by-products and yield of the desired product is low. Furthermore, in the two-step processes ② and ③, by-production of alcohols is inhibited and yield of the desired product can be improved, but is not yet satisfactory.

The inventors have found that yield of the desired product can be further improved by using active carbon as the catalyst for production of imino derivatives and accomplished the present invention.

That is, the present invention provides an industrially excellent process for production of amines by reductive amination of cyclic ketones to the corresponding amines, characterized in that cyclic ketones are allowed to react with ammonia in the presence of active carbon to produce imino derivatives of the ketones and then the resulting imino derivatives are allowed to react with hydrogen in the presence of a hydrogenating catalyst.

The present invention will be explained in more detail.

Production of imino compounds from cyclic ketones

The active carbon used as a catalyst in this step may be any of those which are originated from plants, coals, petroleums and others. Preferred are those which have a large surface area. For example, active carbons having about 800–2000 m$^2$/g of a specific surface area and about 0.4–0.8 ml/g of a pore volume are generally used. Active carbon may be treated with acid or alkali.

The cyclic ketones include alicyclic ketones of 5–20 carbon atoms such as cyclopentanone, cyclohexanone, cycloheptanone, isophorone and 3-cyano-3,5,5-trimethylcyclohexanone and heteroalicyclic ketones of 4–20 carbon atoms such as piperidone, 2,2,6,6-tetramethyl-4-piperidone and 5-benzyl-7-oxo-5-azaspiro[2.4]heptane. They are not limitative.

Production of imino derivatives from cyclic ketones is conducted by allowing cyclic ketones to react with ammonia in a batch or flow system. The latter is preferred. In the case of the flow system, a fixed-bed liquid-phase flow system is usually employed in either an up-flow or a down-flow system.

Reaction temperature is usually 0°–100° C. Reaction pressure is usually from a pressure under which ammonia liquefies at the reaction temperature to about 300 atm. Especially high pressure is not needed, but the pressure may be the same as in the subsequent hydrogenating step.

Amount of ammonia is usually about 1–60 mols per mol of the cyclic ketone used, and preferably 2–50 mols when the reaction mass is supplied, as it is, to the subsequent hydrogenating step.

Amount of the catalyst is usually 1–25% by weight against the cyclic ketone and reaction time is usually about 5 minutes to 3 hours in the batch system. Feed rate of the starting ketone in flow system is usually about 0.05–15 h$^{-1}$, preferably 0.1–10 h$^{-1}$ in LHSV.

The production of imino derivatives may also be carried out in the presence of a solvent. Examples of the solvent are alcohols such as methanol, ethanol, propanol, ethylene glycol and ethylene glycol monomethyl ether, ethers such as diethyl ether, tetrahydrofuran, dioxane and ethylene glycol dimethyl ether, hydrocarbons such as hexane and heptane, and mixtures thereof. Methanol is preferred.

Amount of the solvent is usually 0.5–10 parts by weight based on one part by weight of the cyclic ketone.

An imino derivative produced is usually supplied, as it is, to the subsequent hydrogenating step without being isolated, after the catalyst has been separated from the reaction mass. Alternatively, isolation of the imino derivative may be made, before it is supplied to the hydrogenating step.

Hydrogenation of the imino derivative

The hydrogenation is carried out with hydrogen in the presence of a catalyst.

Examples of the catalyst are nickel catalysts such as reduced nickel and Raney nickel, cobalt catalysts such as reduced cobalt and Raney cobalt, and noble metal catalysts such as ruthenium, rhodium, palladium, platinum and iridium. These catalysts may be supported on carriers. Furthermore, for example, reduced cobalt or Raney cobalt to which is added ruthenium, rhodium, manganese, zirconium or copper may be used.

The hydrogenation reaction is carried out by a batch system or a flow system. The latter is preferred. In the case of the flow system, the fixed-bed liquid-phase flow system, either up-flow or down-flow is usually employed.

Reaction temperature is usually 0°–200° C., preferably 30°–130° C. Reaction pressure is usually from a pressure under which ammonia liquefies at the reaction temperature to about 300 atm.

Ammonia is generally added in an amount of about 1–60 mols, preferably 5–50 mols per mol of the imino derivative for inhibiting production of byproducts.

Amount of the catalyst is usually 0.01–5 parts by weight based on one part by weight of the imino derivative and reaction time is usually about 30 minutes to 10 hours, in the case of batch method. Feed rate of the imino derivative in the case of flow method is usually about 0.01–10 h$^{-1}$, preferably 0.02–5 h$^{-1}$ in LHSV.

The hydrogenation may also be carried out in the presence of a solvent. Examples of the solvent are alcohols such as methanol, ethanol, propanol, ethylene glycol and ethylene glycol monomethyl ether, ethers such as diethyl ether, tetrahydrofuran, dioxane and ethylene glycol dimethyl ether, hydrocarbons such as hexane and heptane, and mixtures thereof. Methanol is preferred. Amount of the solvent is usually 0.5–10 parts by weight based on one part by weight of the cyclic ketone.

Amount of hydrogen in the case of batch system depends on the reaction pressure and is usually 300 atm or lower. Amount of hydrogen in the case of flow system is 1–30 mol times as much as the theoretical amount required for a material to be reduced.

Recovery of amines

Amine produced may usually be isolated by separation such as distillation after the catalyst has been removed from the reaction mass. If necessary, the amine is further purified by purification such as rectification and recrystallization.

According to the present process, amines are produced from the corresponding cyclic ketones in high yield by using active carbons as a catalyst for production of imino derivatives.

The following nonlimiting examples explain the present invention in more detail.

EXAMPLE 1

A stainless steel reaction tube (1) (50 cm in length, 9 mm in inner diameter) packed with 4.6 g of active carbon [10–20 mesh, GVA-S manufactured by Tsurumi Coal Co., Ltd., .(specific surface area: 1667 m$^2$/g, pore volume: 0.75 ml/g (nitrogen gas adsorbing method))] and a stainless steel reaction tube (2) (50 cm in length, 9 mm in inner diameter) packed with 18.5 g of cobalt catalyst and supported on silica (10–20 mesh, G-103 manufactured by Nissan Girdler Co., Ltd.) which is previously reduced with hydrogen were vertically provided and the top of the reaction tube (1) was connected with the bottom of the reaction tube (2). Then, a mixture of 3-cyano-3,5,5-trimethylcyclohexane (IPCN), methanol and liquid ammonia (1:1:2.5 in weight ratio) was fed at 16.6 g/h from the bottom of the reaction tube (1). Hydrogen was fed at 7.7 l/h from the bottom of the reaction tube (2).

The temperature was adjusted so that inner temperature of the reaction tubes (1) and (2) reached 20° C., and 114° C. respectively and the pressure of the reaction tubes (1) and (2) was kept at 70 kg/cm$^2$G.

After lapse of 280 minutes from starting of feeding, sampling was carried out from outlets of the reaction tubes (1) and (2) and the samples were analyzed by gas chromatography.

Yield of the IPCN imino derivative at the outlet of the reaction tube (1) was 97.8%. The reaction mixture at the outlet of the reaction tube (2) contained 95.3 wt% of 3-aminomethyl-3,5,5-trimethylcyclohexylamine (IPDA) and 0.4 wt% of 3-aminomethyl-3,5,5-trimethylcyclohexyl alcohol (IPAA), and IPCN and IPCN imino derivative were not detected, Yield of IPDA was 94.9%.

EXAMPLE 2

The procedure of Example 1 was repeated except that in place of the one stainless steel reaction tube packed with cobalt catalyst, two reaction tubes (2) and (3) which were the same as the said stainless steel reaction tube used in Example 1 and connected in series were used; the mixture of IPCN, methanol and liquid ammonia was fed at 16 g/h; hydrogen was fed at 7.5 l/h from the bottom of the reaction tube (2); the inner temperatures of the reaction tubes (2) and (3) were 70° C., and 114° C. respectively; and the pressure was kept at 150 kg/cm$^2$G.

Yield of the IPCN imino derivative at the outlet of the reaction tube (1) was 97.5%. The reaction mixture at the outlet of the reaction tube (3) contained 96.5 wt% of IPDA and 0.3 wt% of IPAA, and IPCN and IPCN imino derivative were not detected. Yield of IPDA was 96.2%.

EXAMPLE 3

In a 120 ml autoclave were charged 1.2 g of active carbon of 32–60 mesh (GVA-S manufactured by Tsurumi Coal Co., Ltd.), 5.04 g of IPCN and 10.1 g of methanol and the autoclave was closed. Then, atmosphere in the autoclave was replaced with nitrogen and 12.6 g of liquid ammonia was injected thereinto. The autoclave was kept at 60° C. for 60 minutes and then cooled to room temperature. Yield of the imino derivative was 96%.

In nitrogen atmosphere, 4.7 g (in terms of Co) of Raney cobalt catalyst (Z-4661 manufactured by Nacalai Tesque Co., Ltd.) and 10 g of methanol were charged in a 120 ml autoclave and the autoclave was closed. Then, the reaction mixture obtained above (containing 0.77 mol of IPCN, 18.5 mmol of IPCN imino derivative, 6.4 g of methanol and 8 g of ammonia) was filtrated under pressure: and injected into the autoclave and then, hydrogen was injected, and reaction was allowed to proceed at 100° C., for 2 hours and under 70 kg/cm$^2$G.

The resulting reaction mixture contained 94.8 wt% of IPDA and 1.6 wt% of IPAA, and IPCN and IPCN imino derivative were not detected. Yield of IPDA was 94.4%.

EXAMPLE 4

The procedure of Example 1 was repeated except that active carbon was used in an amount of 7.7 g (20 ml) and the cobalt catalyst was used in an amount of 20.6 g (20 ml); a mixture of IPCN and methanol (1:1.5 in weight ratio) and liquid ammonia were fed at 24.8 g/h and 26.1 g/h,, respectively to the bottom of the reaction tube (1); hydrogen was fed at 15 l/h from bottom of the reaction tube (2); and the pressure was kept at 150 kg/cm$^2$G.

Yield of the imino derivative at the outlet of the reaction tube (1) was 97.9%. The reaction mixture at the outlet of the reaction tube (2) contained 93.8 wt% of IPDA and 2.0 wt% of IPAA, and IPCN and IPCN imino derivative were not detected. Yield of IPDA was 93.4%.

EXAMPLE 5

The procedure of Example 4 was repeated except that the mixture of IPCN and methanol (1:1.5 in weight ratio) was fed at 10 g/h, liquid ammonia was fed at 10 g/h and hydrogen was fed at 6 l/h and the pressure was kept at 70 kg/cm$^2$G.

Yield of the imino derivative at the outlet of the reaction tube (1) was 97.7%. The reaction mixture at the outlet of the reaction tube (2) contained 97.2 wt% of IPDA and 1.9 wt% of IPAA, and IPCN and IPCN imino derivative were not detected. Yield of IPDA was 92.2%.

EXAMPLE 6

The procedure of Example 4 was repeated except that 2,2,6,6-tetramethyl-4-piperidone was used in place of IPCN.

Yield of the imino derivative at the outlet of the reaction tube (1) was 85.2% and that of the amino derivative at the outlet of the reaction tube (2) was 62.9%.

Comparative Example 1

The procedure of Example 1 was repeated except that 6.6 g of active alumina (NKHD-24 manufactured by Sumitomo Chemical Co., Ltd.) was used in place of active carbon.

Yield of the IPCN imino derivative at the outlet of the reaction tube (1) was 77.4%. The reaction mixture at the outlet of the reaction tube (2) contained 87.3 wt% of IPDA and 7.4 wt% of IPAA, and IPCN and IPCN imino derivative were not detected. Yield of IPDA was 86.9%.

Comparative Example 2

The procedure of Example 4 was repeated except that 11.5 g (20 ml) of ion exchange resin (Amberlyst 15 manufactured by Organo Co., Ltd.) was used in place of active carbon.

Yield of the IPCN imino derivative at the outlet of the reaction tithe (1) was 77.4%. The reaction mixture at the outlet of the reaction tube (2) contained 82 wt% of IPDA and 12.1 wt% of IPAA, and IPCN and IPCN imino derivative were not detected. Yield of IPDA was 81.5%.

Comparative Example 3

The procedure of Example 4 was repeated except that 13.2 g (20 ml) of active alumina (NKHD-24 manufactured by Sumitomo Chemical Co., Ltd.) was used in place of active carbon.

Yield of the IPCN imino derivative at the outlet of the reaction tube (1) was 60.3%. The reaction mixture at the outlet of the reaction tube (2) contained 61.4 wt% of IPDA and 35.4 wt% of IPAA, and IPCN and IPCN imino derivative were not detected. Yield of IPDA was 61.4%.

Comparative Example 4

The procedure of Example 6 was repeated except that 11.5 g (20 ml) of ion exchange resin (Amberlyst 15 manufactured by Organo Co., Ltd.) was used in place of active carbon.

Yield of the imino derivative at the outlet of the reaction tube (1) was 80.9%. Yield of the amino derivative at the outlet of the reaction tube (2) was 54.3%.

Comparative Example 5

The procedure of Example 6 was repeated except that 13.2 g (20 ml) of active alumina (NKHD-24 manufactured by Sumitomo Chemical Co., Ltd.) was used in place of active carbon.

Yield of the imino derivative at the outlet of the reaction tube (1) was 17.9% and yield of amino derivative at the outlet of the reaction tube (2) was 22.4%.

We claim:

1. A process for producing an amine by carrying out reductive amination of a cyclic ketone to the corresponding amine which comprises allowing a cyclic ketone to react with ammonia in the presence of a catalyst consisting essentially of active carbon to produce an imino derivative and then, allowing the imino derivative to react with hydrogen in the presence of a hydrogenating catalyst.

2. A process according go claim 1, wherein the active carbon has 800-2000 $m^2/g$ of a specific surface area.

3. A process according to claim 1, wherein the active carbon has 0.4-0.8 ml/g of a pore volume.

4. A process according to claim 1, wherein the cyclic ketone is an alicyclic or heteroalicyclic ketone having 4-20 carbon atoms in total.

5. A process according to claim 4, wherein the alicyclic ketone is at least one ketone selected from cyclopentanone, cyclohexanone, cycloheptanone, isophorone and 3-cyano-3,5,5-trimethylcyclohexanone.

6. A process according to claim 4, wherein the alicyclic ketone is 3-cyano-3,5,5-trimethylcyclohexanone.

7. A process according to claim 4, wherein the heteroalicyclic ketone is at least one ketone selected from piperidone, 2,2,6,6-tetramethyl-4-piperidone and 5-benzyl-7-oxo-5-azaspiro[2.4]heptane.

8. A process according to claim 4, wherein the heteroalicyclic ketone is 2,2,6,6-tetramethyl-4-piperidone.

9. A process according to claim 1, wherein amount of ammonia is 1-60 mols per mol of the cyclic ketone.

10. A process according to claim 1, wherein active carbon is used in an amount of 1-25 wt% based on the cyclic ketone.

11. A process according to claim 1, wherein the reaction of the cyclic ketone with ammonia is carried out at a temperature in the range of 0°-100° C. and under a pressure in the range of from a pressure under which ammonia liquefies to 300 atm.

12. A process according to claim 1, wherein feed rate of the cyclic ketone is 0.05-15 $h^{-1}$ in LHSV.

13. A process according to claim 1, wherein the reaction of the cyclic: ketone with ammonia is carried out in the presence of an alcohol solvent, an ether solvent, a hydrocarbon solvent or a mixture thereof.

14. A process according to claim 13, wherein the alcohol solvent is methanol.

15. A process according to claim 13, wherein amount of the solvent is 0.5-10 parts by weight based on the cyclic ketone.

16. A process according to claim 1, wherein the imino derivative produced is fed, as it is, to the hydrogenating step without being isolated after the catalyst is removed from reaction mass, 17. A process according to claim 1, wherein the hydrogenating catalyst is at least one catalyst selected from reduced nickel, Raney nickel, reduced cobalt, Raney cobalt, ruthenium, rhodium, palladium, platinum and iridium.

18. A process according to claim 1, wherein the hydrogenating catalyst is used in an amount of 0.01-5 parts by weight based on the imino derivative.

19. A process according to claim 1, wherein the hydrogenation is carried out at a temperature in the range of 0°-200° C. and under a pressure in the range of from a pressure under which ammonia liquefies to 300 atm.

20. A process according to claim 1, wherein feed rate of the imino derivative is 0.01-10 $h^{-1}$ in LHSV.

21. A process according to claim 1, wherein the hydrogenation of the imino derivative is carried out in the presence of an alcohol solvent, an ether solvent, a hydrocarbon solvent or a mixture therof.

22. A process according to claim 21, wherein the alcohol solvent is methanol.

23. A process according to claim 21, wherein amount of the solvent is 0.5–10 parts by weight based on the imino derivative.

24. A process according to claim 1, wherein amount of hydrogen is 1–30 mol times as much as the theoretical amount required for a material to be reduced.

25. A process for producing an amine by carrying out reductive amination of a cyclic ketone to the corresponding amine which consists essentially of allowing a cyclic ketone to react with ammonia in the presence of active carbon to produce an imino derivative and then, allowing the imino derivative to react with hydrogen in the presence of a hydrogenating catalyst.

* * * * *